United States Patent [19]

Howell

[11] 4,000,738
[45] Jan. 4, 1977

[54] PARENTERAL FLUID ADMINISTRATION SET (PLASTIC-BAG TYPE)

[76] Inventor: William L. Howell, 3615 Macomb St. NW., Washington, D.C. 20016

[22] Filed: Dec. 19, 1975

[21] Appl. No.: 642,365

[52] U.S. Cl. .......................... 128/214 D; 128/228; 128/272; 137/135; 222/106; 222/416

[51] Int. Cl.² .......................................... A61M 5/14

[58] Field of Search ....... 128/214 R, 214 C, 214 D, 128/214.2, 227, 228, 272; 137/123, 130–131, 135, 142, 149, 150, 152–153, 578; 222/67, 92, 106, 107, 204, 416

[56] References Cited

UNITED STATES PATENTS

| | | | |
|---|---|---|---|
| 2,542,461 | 2/1951 | Bay | 128/228 |
| 2,640,358 | 6/1953 | McClure et al. | 222/416 X |
| 2,648,333 | 8/1953 | Cutter | 128/214 C |
| 2,786,467 | 3/1957 | Price | 128/214 D |
| 2,848,995 | 8/1958 | Ryan | 128/214 D |
| 3,030,952 | 4/1962 | Elder | 128/214 D |
| 3,949,745 | 4/1976 | Howell | 128/214 C |

Primary Examiner—Dalton L. Truluck
Attorney, Agent, or Firm—J. Harold Kilcoyne

[57] ABSTRACT

A parenteral fluid administration set comprising a plastic bag adapted to be supplied with a predetermined quantity of the parenteral fluid, said bag being foldable over on itself about a transverse fold-over line, a floating siphon enclosed within the plastic bag adapted to follow the level of the parenteral fluid supplied thereto, said floating siphon being adapted to be forced relatively downwardly to substantially its lowermost position in the plastic bag responsive to folding over of the upper portion of said bag on its lower end portion about said fold-over line, thereby immersing the float of the floating siphon in fluid contained in its lower end, as effects conditioning of the floating siphon for operation, the outlet leg of the siphon terminating in a fluid outlet end, said floating siphon being rendered operative to dispense fluid from the plastic bag through said siphon outlet end upon the plastic bag being unfolded and suspended from its upper end.

7 Claims, 2 Drawing Figures

U.S. Patent  Jan. 4, 1977  4,000,738
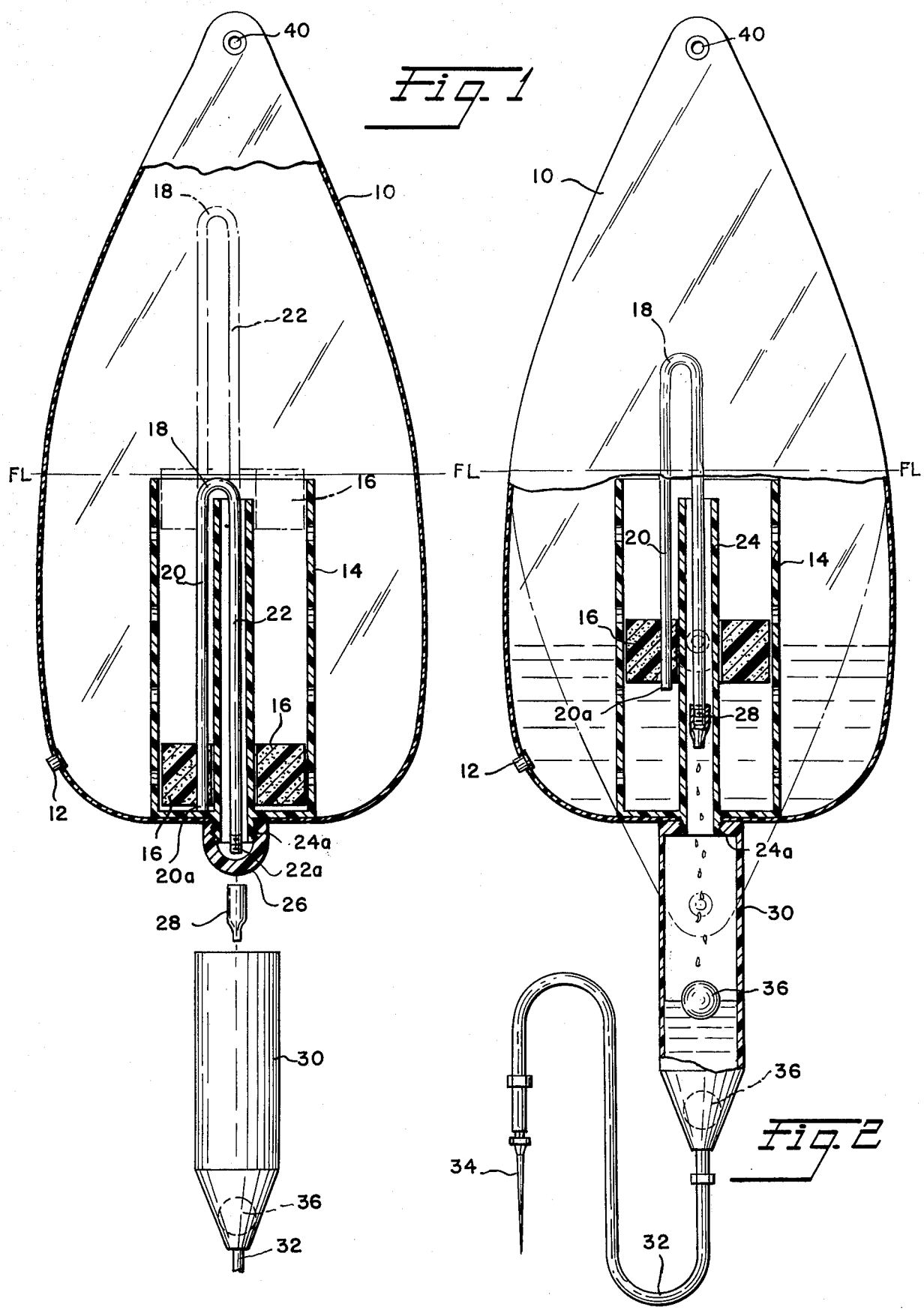

PARENTERAL FLUID ADMINISTRATION SET (PLASTIC-BAG TYPE)

THE INVENTION — IN GENERAL

The present invention relates to means for dispensing parenteral fluids for intravenous administration from a plastic-bag source of supply thereof, as distinguished from the more conventional bottle, to an intravenous tubing line at a controllable uniform rate, comprising a floating siphon-type flow regulator enclosed in said bag an immersed in the parenteral fluid contained therein and which is conditioned for operation by folding one end portion of the plastic bag over on itself and is rendered operative responsive to the bag being hung from its said folded-over end upon unfolding thereof, and to the opening of a normally closed fluid-exit nipple disposed at its opposite end.

BACKGROUND OF THE INVENTION

It is known to supply parenteral fluids to be administered intravenously in disposable plastic bags, as distinguished from the more conventional bottles, in varying quantities of 1 liter, ½ liter, ¼ liter, and so on. However, such plastic bags, like the bottles which they have superseded to a degree, lack means other than known unsatisfactory clamp means for altering the calibre of the IV tubing line in which the bags are connected, for regulating the rate of fluid flow therefrom. That is to say, despite the need for simple, effective means for dispensing parenteral fluids from a plastic bag containing a supply thereof, up to the present time such need could be satisfied only by the use of electrically powered positive pressure pumps connected to the IV tubing line which are both expensive and cumbersome in use, such necessitating disconnection of the pump motor with the result that flow of the fluid is stopped until another electrical connection is reached. In other situations, it is desirable that the patients be ambulatory, walking halls as when receiving heparin, with the result that the patient's walking is restricted to an area limited by the radius provided by an extension cord.

The net result of the aforesaid lack of simple, effective means insuring uniform flow of parenteral fluids from a source thereof such as a suspended plastic bag has been that uniformity of flow is usually attempted to be attained by frequent visits of a nurse or nurses to the administration set to count the number of drops of the fluid flowing or being dispensed per minute or by the rate of emptying of a small reservoir made a part of the intravenous tubing.

OBJECTS OF THE INVENTION

The present invention aims to provide (and provides) a plastic-bag type dispensing container for parenteral fluids which incorporates means for insuring flow therefrom at a controllable uniform rate to a receiving reservoir which in turn delivers to an IV tubing line and needle, by which latter the fluid is infused into the vein of a patient.

More particularly, the invention has for an object that of providing simple, effective means for insuring a controllable uniform rate of flow of parenteral fluids from a plastic bag utilizing a floating siphon immersed in the fluid contained in the plastic bag and which is conditioned for operation by folding one end portion of said bag over on itself about a transverse line of fold and which fills when the folded plastic bag is laid on its side, i.e. when positioned horizontally, whereby the siphon requires no manual priming.

Yet another important object of the invention is the provision of an intravenous fluid administration set comprising the combination of a plastic-bag type container for the parenteral fluid to be administered, means enclosed in said bag and immersed in said fluid and which is rendered operative to dispense the intravenous fluid therefrom at a controllable uniform rate of flow simply by folding one end portion of the plastic bag over on itself about a fold line extending transversely across the bag, followed by unfolding of the bag and suspending the same from its previously folded-over end, and a receiving reservoir adapted to be coupled to a fluid outlet nipple disposed at the opposite bag end upon disconnection of a closure plug which normally closes said nipple to flow therethrough, and wherein the receiving reservoir delivers to a length of tubing extending to the needle by which the intravenous fluid is infused into the vein of a patient.

A further object of the invention is the provision of a disposable self-contained parenteral fluid administration set as last above set forth and wherein the plastic bag is provided with a hang flap or strap at its upper end enabling same to be suspended from a high-level hook or the like.

A still further yet important object of the invention is the provision of a parenteral fluid administration set which features a floating siphon wholly enclosed within a plastic bag containing a measured quantity of said fluid and which fills when the bag is disposed on its side, and further incorporates means for aseptically altering the calibre of the siphon.

The above and other objects and features of advantage of means for the administration of parenteral fluids for intravenous administration from a plastic-bag source at a controllable rate of flow according to the herein invention will appear from the following drawing figures and detailed description thereof, wherein . .

FIG. 1 is a view in elevation and part-section looking on to a parenteral fluid administration set comprising a plastic bag providing a source of said fluid, the view depicting in full lines a floating siphon disposed within the bag in its lowermost position therein which it would assume when the bag is empty of fluid or when forced to that position by folding-over the bag about a transverse line of fold, the view further showing in broken lines the floating siphon in its uppermost position which it would assume in following the level of the fluid supplied thereto to the level corresponding approximately to that of said fold line, the view further showing the siphon calibre-adjusting tip and the fluid reservoir which are components of the set but which are disconnected from the outlet end of the longer leg of the siphon and the overflow tube outlet nipple, respectively; and FIG. 2 is a generally similar elevation view, with parts shown in section, of the herein parenteral fluid administration set in operation, i.e. dispensing fluid at a controllable constant flow rate from the plastic bag to a reservoir which in turn connects to the IV tubing line extending to an infusion needle.

In said drawing figures, reference numeral 10 designates a plastic bag adapted to contain a measured, known quantity of a parenteral fluid to be administered intravenously which may be introduced therein via a self-closing inlet 12 preferably disposed near the lower end portion of the plastic bag. Mounted in said bag and suitably affixed to the bag bottom is a perforated-wall open-top cylinder 14 serving to guide and protect the float component 16 having annular shape of a floating siphon comprising said float and an inverted U-tube generally designated 18 whose shorter leg 20 extends through and is affixed to said float with its inlet end 20a disposed at a level just below the lower line thereof. The longer leg 22 of said U-tube extends dowwardly from the U-bend thereof through an upright open-ended overflow tube 24 disposed coaxially within the perforated-wall cylinder 14, the lowermost end 24a of which projects a small distance through and beyond the bag bottom and terminates in an outlet nipple which is externally threaded. Said longer leg 22 of the U-tube terminates in a fluid outlet end 22a which is disposed vertically below said inlet end 20a of the shorter leg 20 and which, when the float 16 is in its lowermost position within the protective cylinder 14, extends a short distance beyond the aforesaid nipple end 24a of said overflow tube 24.

Normally, any and all fluid flow through the fluid-outlet end 22a of the siphon U-tube and said outlet nipple 24a is prevented by a removable cup-shaped closure element 26 which is adapted to be screw-threaded to the projecting nipple-end 24a of the overflow tube 24, in the cup recess of which the fluid outlet end 22a of the siphon leg 22 may be accommodated.

To said outlet end 22a of the siphon leg 22 is adapted be fitted a calibre adjusting tip 28 by which the rate of fluid flow from the bag, i.e. in terms of formed drops per unit measure of time may be controlled.

Also adapted to be threadedly connected to the plastic bag 10 via the projecting nipple end 24a of the overflow tube 24 is a receiving reservoir 30 whose lower end portion has gradually decreasing diameter and to whose lower, small diameter end a length of tubing 32 extending to a needle 34 is connected. Operatively disposed in said reservoir is a floating sphere or ball valve 36 which, when the fluid in said reservoir is exhausted, lowers to a position in which it closes off the entrance to tubing 32 and thereby prevents inflow of air.

As shown in FIG. 1, the plastic bag 10 is adapted to be hung from its upper end portion, and for this purpose is provided adjacent said upper end with a grommet 40 or the like for the passage of a hook (not shown) from which the bag may be suspended.

However, it is a feature of the invention that the plastic bag 10 as supplied will be disposed on its side and will contain a predetermined quantity of a parenteral fluid (and such medication as is to be administered therewith) introduced through the inlet 12, up to the approximate level of the upper end of the overflow tube 24. Further, as so supplied, the upper end portion of the plastic bag 10 will be folded over on and lightly sealed to the lower end portion thereof, about a transverse line of fold designated FL. Alternatively, the plastic bag may be first folded over about said line of fold, lightly sealed in folded-over position, and then filled with the fluid to be administered.

As seen in FIG. 2, said transverse line of fold is disposed approximately midway of the length of the plastic bag, and consequent to the over-folding thereof as aforesaid, the siphon U-tube 18 and the float 16 are forced downwardly in unison within the perforated-wall protective cylinder 14 to their lowermost position in said cylinder, being thus immersed in any fluid content of the bag. Also, consequent to the siphon and float being so immersed in fluid, the siphon tube fills without any requirement for priming same.

It is preferred that up to this stage of use or operation the cup-shaped closure element 26 is screw-threaded to the projecting nipple 24a, thus closing off any flow of the fluid from the plastic bag through the outlet end 22a of the longer siphon leg. That is to say, that while the folding-over of the upper end portion of the bag conditions the floating siphon for operation by forcing same to its lowermost possible immersed position within the perforated wall cylinder 14, fluid flow is still precluded by said closure element 26.

To render the siphon operative, the folded-over end of the bag is unfolded and is hung from a high-level hook or the like. Thereupon, the closure element 26 is unscrewed from the projecting nipple end 24a of the over flow tube 24, being replaced with the calibre adjusting tip 28 and the receiving reservoir 30, whereupon the floating siphon will gradually rise to its broken-line position shown in FIG. 1, or to some intermediate position depending on the quantity of fluid supplied to and/or remaining in the bag.

With the siphon already primed as aforesaid, parenteral fluid from the bag will flow therefrom at a constant drop-rate determined by either a previous (initial) setting of the siphon-bore calibre altering means 28, or by adjusting the calibre of the siphon as may be desired by the squeeze pressure applied thereto via the wall structure of the reservior 30, which is fashioned from a deformable-reformable plastic capable of transmitting squeeze pressure to the calibre adjusting tip, and thereupon reforming to its initial configuration.

From the foregoing, it will be appreciated that a parenteral fluid administration set according to the herein invention fulfills a long-felt want and need in the art for a parenteral fluid administration set employing a plastic bag source of the fluid, capable of dispensing the fluid and/or added medicament from the plastic bag at a constant controllable rate to a reservoir connected in the IV tubing line extending from the plastic bag and reservoir to the infusion needle by which the fluid is administered to a patient, which is simple and inexpensive in its construction, highly accurate and effective in its operation, and which features a floating siphon possessing the ability of priming itself automatically when the plastic bag is turned or laid on its side, and also incorporating means for aseptically altering the calibre of the siphon bore through which the fluid is dispensed from the plastic bag.

Accordingly, the features representative of the spirit and structure of the invention are defined with particularity in the appended claims

I claim:

1. A parenteral fluid administration set comprising a plastic bag adapted to be filled with a parenteral fluid to be administered intravenously up to the approximate level of a fold-over line extending transversly across the bag, said bag having an outlet opening and a tubing line extending therefrom to an infusion needle, a floating siphon in said bag adapted to be immersed in said fluid when the bag is so filled, said siphon having fluid inlet and fluid outlet legs, said outlet leg having an end extending through said outlet opening and providing a fluid outlet from said bag, means including a receiving reservoir affixed to said bag outlet and depending from said bag and being connected to said tubing line which in turn is connected to said infusion needle, means for conditioning the floating siphon for operation, and means for rendering said floating siphon operative to dispense said fluid through said extending end of said siphon outlet leg to said receiving reservoir at a controllable constant rate.

2. A parenteral fluid administration set according to claim 1, wherein said fold-over line is at a level determining the maximum upward position of the floating siphon.

3. A parenteral fluid administration set accord-to claim 1, including a fluid overflow tube within said bag connected to said bag outlet opening, and wherein said fold-over line is disposed at the approximate level of the upper end of said overflow tube, the lower end of said overflow tube projecting through the bag bottom and said receiving reservoir being coupled to said projecting end.

4. A parenteral fluid administration set according to claim 1, wherein said means for conditioning the floating siphon for operation comprises a fold-over relatively upper end portion of the plastic bag and which is adapted, when folded over on to the lower end portion of the bag, to exert relative downward force on the floating siphon as affects its immersion in the fluid supplied to said bag.

5. A parenteral fluid administration set according to claim 1, and wherein the means for rendering the so-conditioned floating siphon operative comprises means for suspending the bag from the upper end upon unfolding the same as enables the floating siphon to follow the level of the fluid as it lowers with fluid flow therefrom.

6. A parenteral fluid administration set according to claim 3, wherein the overflow tube is disposed coaxially within an open-top perforated-wall cylinder affixed to the bottom of the plastic bag, and wherein said floating siphon moves vertically within the perforated-wall cylinder in following the level of the fluid supplied to the bag.

7. A parenteral fluid administration set for dispensing fluid from a plastic bag source thereof at a controllable constant rate including, in combination:
 a plastic bag adapted to be folded on itself about a transverse line of fold;
 a perforated-wall open-top cylinder affixed to the bottom of the plastic bag and extending relatively upwardly therefrom to approximately the transverse line of fold;
 a coaxial open-ended overflow tube within said cylinder, the lower end of which extends through and terminates a small distance relatively below said bag bottom;
 a readily removable closure element normally closing said extending end of the overflow tube;
 a floating siphon comprising a float and a siphon affixed to said float disposed within said perforated-wall cylinder for vertical movement in accordance with fluid level in the bag and cylinder, one leg of the siphon extending through the float and terminating in a fluid inlet end and the other leg of the siphon extending downwardly through said open-ended overflow tube and terminating in a fluid outlet end;
 means attachable to said outlet end for altering the calibre of said siphon and thereby the rate of flow therethrough;
 the construction and arrangement being such that folding-over of the upper end of the bag on itself conditions the floating siphon for operation and subsequent unfolding of and suspending the bag from its previously folded-over end, coupled with removal of said closure element from the extended end of the overflow tube and attachment of said calibre altering means renders the floating siphon operative to dispense fluid from said plastic bag at a rate determined by said calibre altering means.

* * * * *